United States Patent [19]

Welstead, Jr.

[11] 4,001,429
[45] Jan. 4, 1977

[54] 1-CYCLOPROPYL-1-PHENYL-ω-AMINO-1-ALKANOLS AND 1-LOWER-ALKYLACYL DERIVATIVES AS ANALGETICS

[75] Inventor: William John Welstead, Jr., Richmond, Va.

[73] Assignee: A. H. Robins Company, Inc., Richmond, Va.

[22] Filed: Apr. 28, 1975

[21] Appl. No.: 580,106

Related U.S. Application Data

[62] Division of Ser. No. 456,940, April 1, 1974, Pat. No. 3,928,426, which is a division of Ser. No. 221,804, Jan. 28, 1972, abandoned.

[52] U.S. Cl. .............................. 424/311; 424/267
[51] Int. Cl.$^2$ ............... A61K 31/22; A61K 31/445
[58] Field of Search ............................ 424/330, 311

[56] References Cited

UNITED STATES PATENTS

| | | | |
|---|---|---|---|
| 3,065,261 | 11/1962 | Stephens | 260/490 |
| 3,652,589 | 3/1972 | Flick et al. | 260/490 |
| 3,714,229 | 1/1973 | Saari et al. | 260/490 |

*Primary Examiner*—Stanley J. Friedman

[57] ABSTRACT

Novel 1-cyclopropyl-1-phenyl-ω-amino-1-alkanols and 1-lower-alkylacyl derivatives are described having the formula:

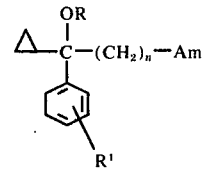

wherein;

A$m$ is lower-alkylamino, di-lower-alkylamino and piperidino, R is hydrogen and lower alkanoyl, R$^1$ is hydrogen, halogen, lower-alkoxy, lower-alkyl and trifluoromethyl, and $n$ is two and three. The compounds wherein R is hydrogen have antidepressant properties and those wherein R is lower-alkanoyl have analgetic properties.

3 Claims, No Drawings

1-CYCLOPROPYL-1-PHENYL-ω-AMINO-1-ALKANOLS AND 1-LOWER-ALKYLACYL DERIVATIVES AS ANALGETICS

The present application is a division of application Ser. No. 456,940, filed Apr. 1, 1974, now U.S. Pat. No. 3,928,426, which is a division of application Ser. No. 221,804, filed Jan. 28, 1972, and now abandoned.

The present invention relates to novel tertiary alcohols and lower-alkylacyl derivatives thereof and is more particularly concerned with 1-cyclopropyl-1-phenyl-ω-amino-1-alkanols and 1-cyclopropyl-1-phenyl-ω-amino-1-loweralkanoyloxyalkanes and methods of making and using the same.

The novel compounds can be represented by the formula:

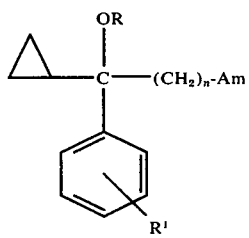

Formula I wherein;

A$m$ is lower-alkylamino, di-lower-alkylamino and piperidino,

R is hydrogen and lower-alkanoyl, $R^1$ is hydrogen, halogen, lower-alkoxy, lower-alkyl and trifluoromethyl, n is two and three, and the pharmaceutically acceptable acid addition salts thereof.

The novel compounds of the invention having the foregoing Formula I wherein R is hydrogen are generally characterized by important pharmacological activity and exhibit central nervous system activity. More specifically, the present compounds can be used as anti-depressants.

The activity of the compounds was determined by their administration intraperitoneally to mice and their effectiveness in blocking the depressant effects which are induced in mice by the intravenous administration of 2-oxo-3-insobutyl-9,10-dimethoxy-1,2,3,4,6,7-hexahydro-11bh-benzo[a]quinolizine (tetrabenazine). The procedure used was a modification of Englehardt, E. L. et al, J. Med. Chem. 11 (2), 325(1968). The $ED_{50}$ values of the compounds are given in Table I; the compounds of Examples 3, 5, 7 and 8 are the preferred compounds.

TABLE I

| Example | $ED_{50}$ mg/kg, IP |
|---|---|
| 1 | 10.0 |
| 2 | 12.5 |
| 3 | 6.4 |
| 4 | 7.8 |
| 5 | 2.5 |
| 6 | 12.0 |
| 7 | 4.2 |
| 8 | 4.6 |
| 10 | 7.7 |

The compounds of the invention having the foregoing Formula I wherein R is lower-alkanoyl have been shown to posssess analgesic properties.

The analgesic activity of the 1-cyclopropyl-1-alkanoyloxy-1-phenyl-ω-amino alkane compounds of this invention were determined by a modification of Nilsen's method [Funderburk, W. H., et al, Arch. Int. Pharmacodynamie 178, 446–456(1969)]. The $ED_{50}$ analgetic dose administered intraperitoneally to mice was 14.2 mg/kg for the preferred compound of Example 10.

It is, accordingly, an object of the present invention to provide new and useful 1-cyclopropyl-1-phenyl-ω-amino-1-alkanols and 1-cyclopropyl-1-phenyl-ω-amino-1-lower-alkanoyloxyalkanes and methods of making and using the same. Other objects of the invention will be apparent to one skilled in the art, and still other objects will become apparent hereinafter.

In the definition of symbols in the foregoing Formula I and where they appear elsewhere throughout this specification, the terms have the following significance.

The term "lower-alkyl" as used herein includes straight and branched chain radicals of up to eight carbon atoms inclusive and is exemplified by such group as methyl, ethyl, propyl, isopropyl, tertiary butyl, butyl, amyl, isoamyl, hexyl, heptyl, octyl, and the like. "Lower-alkoxy" has the formula -O-lower-alkyl. The term "lower-alkanoyloxy" has the formula -O-C(O)-lower-alkyl.

The term "phenyl" is meant to include both the unsubstituted phenyl radical and the monosubstituted phenyl radical. The preferred monosubstituents are halides, lower-alkyl radicals, lower-alkoxy radicals, and the trifluoromethyl radical.

The invention also contemplates the pharmaceutically acceptable acid addition salts of the bases of the foregoing Formula I and includes both inorganic and organic salts as exemplified by those prepared with inorganic acids such as hydrochloric, hydrobromic, sulfuric and sulfamic and with strong organic acids such as fumaric, maleic, tartaric and oxalic acid. The preferred acid addition salt is the hydrochloride.

METHOD OF PREPARATION

The preparation of the 1-cyclopropyl-1-phenyl-ω-amino-1-alkanols (I) may be accomplished by mixing and reacting 1-cyclopropyl-3-amino-1-propanones (II) with appropriately substituted phenyl Grignards (III) and/or phenyllithium compounds (III) and by reacting cyclopropylphenyl ketone (IV) with an ω-aminopropylmagnesium halide (V). The reaction sequences are illustrated by the following:

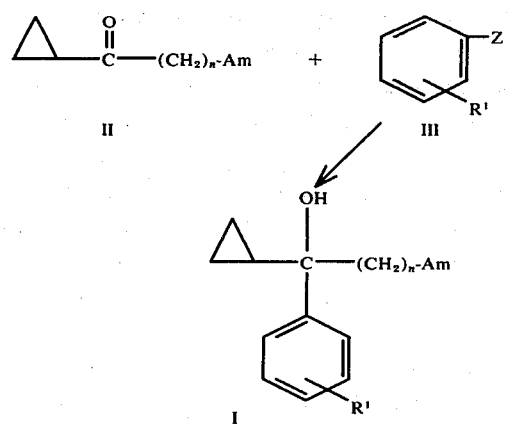

wherein Am, n and R¹ have the values previously assigned and Z is -Mg halide and Li; and

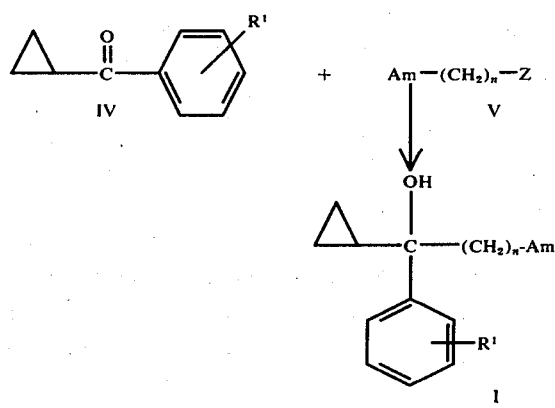

wherein Am and R¹ have the values previously assigned, Z is -Mg-halide and n is three.

A general procedure for the preparation of the 1-cyclopropyl-1-phenyl-ω-amino-1-propanols (I) by reaction with a Grignard compound and/or phenyllithium is described below.

An appropriately substituted phenyl Grignard compound or phenyllithium is prepared in a dry organic solvent as, for example, ether or tetrahydrofuran and the metallo organic compound is treated in the cold, preferably at −20° C to 30° C., with a 1-cyclopropyl-3-amino-1-propanone. The reaction mixture is allowed to warm to ambient temperature and the reaction complex is carefully decomposed using a dilute aqueous acidic solution such as aqueous ammonium chloride solution. The organic phase containing the product is worked up by methods known to the art. The product which is usually an oil is converted to a suitable acid addition salt.

A general procedure for the preparation of a 1-cyclopropyl-1-phenyl-ω-amino-1-lower-alkanoyloxyalkane is to dissolve the 1-cyclopropyl-1-phenyl-ω-amino-1-alkanol in a suitable solvent, illustratively chloroform, containing a metal carbonate such as potassium carbonate and treating the chloroform solution in the cold (0° C.) with a suitable lower-alkanoyl halide. After the reaction has been completed the products are partitioned between chloroform and water and the chloroform phase containing the 1-cyclopropyl-1-phenyl-ω-amino-1-lower-alkanoyloxyalkane is separated and worked up by methods known to the art. The oily product is converted to a suitable acid addition salt.

The preparations and examples which follow serve to illustrate the invention. It is to be understood that the examples in no way limit the spirit or scope of the invention.

STARTING MATERIALS

The 1-cyclopropyl-3-amino-1-propanones used as starting materials in the present invention were prepared by the Mannich reaction using cyclopropyl methyl ketone, paraformaldehyde and an amine as disclosed in copending application Ser. No. 144,634 filed May 18, 1971. The preparation of 1-cyclopropyl-3-(N-methylacetamido)-1-(m-trifluoromethylphenyl)-1-propanol is shown in Preparation 3.

PREPARATION 1

1-Cyclopropyl-3-methylamino-1-propanone.

A solution of 42.5 g. (0.3 mole) of 1-cyclopropyl-3-dimethylamino-1-propanone in 200 ml. of benzene was refluxed while methylamine was bubbled through the solution for eight hours. The nuclear magnetic resonance spectrum indicated a 90% conversion to 1-cyclopropyl-3-methylamino-1-propanone.

PREPARATION 2

1-Cyclopropyl-3-(N-methylacetamido)-1-propanone.

A crude solution of 1-cyclopropyl-3-methylamino-1-propanone was cooled to 8°–10° C. and 8.2 g. (0.06 mole) of potassium carbonate was added, followed by 50 g. (0.5 mole) of acetic anhydride. The mixture was stirred until it warmed to room temperature. The benzene layer was separated, dried over magnesium sulfate, concentrated, and the residual oil distilled at 99°–150° C./0.1 mm. The distillate weighed 65 g. It was calculated to contain 80% of 1-cyclopropyl-3-(N-methylacetamido)-1-propanone by the nuclear magnetic resonance spectrum.

PREPARATION 3

1-Cyclopropyl-3-(N-methylacetamido)-1-(m-trifluoromethylphenyl)-1-propanol.

An ether solution of a Grignard reagent prepared from 50.0 g. (0.35 mole) of 3-bromobenzotrifluoride, 400 ml. of ether and 8.6 g. (0.354 mole) of magnesium was treated at −20° C to −30° C. with 12.5 g. (0.059 mole) of crude 1-cyclopropyl-3-(N-methylacetamido)-1-propanone (calculated to contain 80% of the propanone by the nuclear magnetic resonance spectrum) in 100 ml. of ether. The rection mixture was warmed to room temperature and treated with 7.4 g. (0.14 mole) ammonium chloride followed by 20 ml. of water. The ether layer was separated, concentrated to a dark oil and distilled under reduced pressure. The yield was 6.2 g.; b.p. 110°–114° C./0.1 mm.

EXAMPLE 1

1-Cyclopropyl-3-dimethylamino-1-phenyl-1-propanol Hydrochloride.

An ethereal solution of phenyllithium (0.2 mole) was prepared in a nitrogen atmosphere using 31.4 g. (0.2 mole) of bromobenzene, 2.8 g. (0.4 mole) of lithium wire and 60 ml. of ether. After stirring overnight the stirred mixture was treated slowly with 24.7 g. (0.175 mole) of 1-cyclopropyl-3-dimethylamino-1-propanone at a temperature below −20° C. After most of the ketone had been added, 50 ml. of ether was added to increase the fluidity. The stirred mixture was allowed to warm to room temperature over a 3-hour period and then poured into ice. The ether layer was separated, dried over magnesium sulfate and evaporated under reduced pressure to give 33 g. of an oil. The oil was distilled in vacuo and the major fraction distilled at 70°–72° C./0.01 mm. (23.5 g.; 61%). The nuclear magnetic resonance spectrum of the oil was consistent with the proposed structure. Vapor phase chromatography gave a single peak. Seven grams of the oil was converted to the hydrochloric salt which was recrystallized from isopropanol-isopropyl ether to give 2.6 g. of the pure salt which melted at 157°–159° C.

Analysis: Calculated for $C_{14}H_{22}ClNO$: C,65.73; H,8.67; N,5.48.

Found: C,65.44; H,8.46; N,5.59.

EXAMPLE 2

1-Cyclopropyl-4-dimethylamino-1-phenyl-1-butanol Hydrochloride.

A tetrahydrofuran solution of a Grignard reagent was prepared from 80.2 g. (0.66 mole) of 3-dimethylaminopropyl chloride, 15.5 g. (0.66 mole) of magnesium metal and 200 ml. of tetrahydrofuran and was treated dropwise with a solution of 46 g. (0.32 mole) of cyclopropyl phenyl ketone in 100 ml. of tetrahydrofuran. After the addition was completed, the mixture was refluxed for one hour, cooled and treated with 300 ml. of water containing 33.7 g. (0.63 mole) of ammonium chloride. The mixture was filtered and the tetrahydrofuran layer was separated from the aqueous layer. The aqueous layer was extracted twice with 100 ml. portions of ether and the extracts were combined with the tetrahydrofuran layer. The solution was dried over magnesium sulfate and concentrated to an oil. The crude oil was distilled in vacuo and the major fraction collected at 90°–96° C./0.14 mm.; the distillate weighed 61 g. (83%). A portion of the base was converted to the hydrochloride salt which melted at 153°–155° C. after recrystallization from isopropanol-isopropyl ether.

Analysis: Calculated for $C_{15}H_{24}ClNO$: C,66.77; H,8.97; N,5.19.

Found: C,66.75; H,8.82; N,5.19.

EXAMPLE 3

1-Cyclopropyl-3-dimethylamino-1-(3-chlorophenyl)-1-propanol Hydrochloride.

An ether solution of a Grignard reagent prepared from 60 g. (0.3 mole) of 3-bromochlorobenzene and 7.2 g. (0.3 mole) of magnesium in 500 ml. of ether was treated at −20° C. to −30° C. with a solution of 21 g. (0.15 mole) of 1-cyclopropyl-3-dimethylamino-1-propanone in 500 ml. of ether. The reaction mixture was allowed to warm to room temperature and was then treated successively with 16 g. of ammonium chloride and 40 ml. of water. The ether layer was decanted and the residue was triturated with several portions of ether. The combined ether solutions were dried over magnesium sulfate and concentrated to an oil. The hydrochloride salt was prepared and was recrystallized from isopropanol-isopropyl ether; the salt melted at 182°–185° C. and weighed 11.5 g. (26.5%).

Analysis: Calculated for $C_{14}H_{21}Cl_2NO$: C,57.94; H,7.29; H,4.83.

Found: C,58.02; H,7.38; N,4.62.

EXAMPLE 4

1-Cyclopropyl-3-dimethylamino-1-(4-methoxyphenyl)-1-propanol Hydrobromide.

The stirred ether solution of the Grignard reagent prepared from 86 g. (0.46 mole) of 4-bromoanisole and 11.2 g. (0.46 mole) of magnesium in 200 ml. of dry ether was treated dropwise with a solution of 30 g. (0.23 mole) of 1-cyclopropyl-3-dimethylamino-1-propanone in 100 ml. of dry ether. After addition the mixture was allowed to warm to room temperature and was then hydrolyzed with water. The mixture was worked up as in Example 1 to give 16 g. (28%) of an oil which distilled at 110°–115° C./0.10 mm. The hydrobromide salt melted at 175°–177° C.

Analysis: Calculated for $C_{15}H_{24}BrNO_2$: C,54.59; H,7.33; N,4.24.

Found: C,54.76; H,7.38; N,4.26.

EXAMPLE 5

1-Cyclopropyl-3-dimethylamino-1-(3-trifluoromethylphenyl)-1-propanol Hydrochloride.

The stirred ether solution of the Grignard reagent prepared from 64 g. (0.28 mole) of 3-bromobenzotrifluoride and 7 g. (0.28 mole) of magnesium was treated at −20° to −30° C. with a solution of 20 g. (0.14 mole) of 1-cyclopropyl-3-dimethylamino-1-propanone in 100 ml. of ether. The mixture was allowed to warm up to room temperature then worked up as in Example 1. Distillation of the crude product gave 10 g. of oil which distilled at 78°–83° C./0.12 mm. The oil was converted to the hydrochloride salt which melted at 170°–172° C. after recrystallization from isopropanol-isopropyl ether; the yield was 8.5 g. (17%).

Analysis: Calculated for $C_{15}H_{21}ClF_3NO$: C,55.64; H,6.54; N,4.33.

Found: C,55.99; H,6.52; N,4.42.

EXAMPLE 6

1-Cyclopropyl-3-dimethylamino-1-(4-trifluoromethylphenyl)-1-propanol Hydrochloride.

The stirred ether solution of the Grignard reagent prepared from 68 g. (0.3 mole) of 4-bromobenzotrifluoride and 7.2 g. (0.3 mole) of magnesium in 500 ml. of dry ether was treated at −20° to −30° C. with 21 g. (0.15 mole) of 1-cyclopropyl-3-dimethylamino-1-propanone. The stirred reaction mixture was allowed to warm up to room temperature and was stirred for an additional two hours. The mixture was treated successively with 16 g. of ammonium chloride and 40 ml. of water. The ether layer was decanted and the residue was triturated with three 200 ml. portions of ether. The combined ether extracts were dried over magnesium sulfate. The hydrochloride salt was prepared and was recrystallized from an isopropanol-isopropyl ether mixture. The salt weighed 10 g. (20.6%) and melted at 204°–205° C. Analysis: Calculated for $C_{15}H_{21}ClF_3NO$: C,55.64; H,6.54; N,4.33.

Found: C,55.63; H,6.60; N,4.17.

EXAMPLE 7

1-Cyclopropyl-3-diethylamino-1-(3-trifluoromethylphenyl)-1-propanol Hydrochloride.

A tetrahydrofuran solution of a Grignard reagent was prepared by the entrainment technique using 8.5 g.

(0.35 mole) of magnesium, 66.5 g. (0.315 mole) of 3-bromobenzotrifluoride, 6.5 g. (0.035 mole) of 1,2-dibromoethane and 300 ml. of tetrahydrofuran. The stirred solution was cooled to 0° C. and was treated over a 20-minute period with a solution of 26 g. (0.15 mole) of 1-cyclopropyl-3-diethylamino-1-propanone in 100 ml. of ether. The reaction mixture was worked up as in Example 1 and the product was distilled under reduced pressure. The fraction which distilled between 105°–125° C./0.4 mm. was dissolved in ether and treated with ethereal hydrogen chloride. The hydrochloride salt was recrystallized from isopropanol-isopropyl ether to give 9 g. (17%) of salt which melted at 123°–124° C.

Analysis: Calculated for $C_{17}H_{25}ClF_3NO$: C,58.03; H,7.16; N,3.98.

Found: C,58.08; H,7.20; N,3.87.

EXAMPLE 8

1-Cyclopropyl-3-methylamino-1-(3-trifluormethylphenyl)-1-propanol.

A mixture of 5 g. (0.016 mole) of 1-cyclopropyl-3-(N-methylacetamido)-1-(3-trifluoromethylphenyl)-1-propanol, 2.9 g. (0.024 mole) of potassium tertiary butoxide and 25 ml. of dimethyl sulfoxide was warmed on a steam bath for 45 minutes. The mixture was cooled, poured into ice water and extracted with benzene. The benzene extract was dried over magnesium sulfate and concentrated to an oil which was distilled at 108° C./0.15 mm. The yield was 2.6 g. (59%).

Analysis: Calculated for $C_{14}H_{18}F_3NO$: C,61.53; H,6.63; N,5.13.

Found: C,61.73; H,6.59; N,4.95.

EXAMPLE 9

1-Cyclopropyl-3-piperidino-1-(3-trifluoromethylphenyl)-1-propanol Hydrochloride.

A stirred ether solution of a Grignard reagent prepared from 14.5 g. (0.6 mole) of magnesium, 136 g. (0.6 mole) of 3-bromobenzotrifluoride and 800 ml. of dry ether treated at −20° C. to −30° C. with 53.5 g. (0.296 mole) of crude 1-cyclopropyl-3-piperidino-1-propanone in 200 ml. of ether. After addition the reaction mixture was stirred and allowed to warm to room temperature over one hour. The reaction mixture was treated with 32 g. of ammonium chloride in 170 ml. of water and the ether layer separated. The aqueous fraction was filtered and the solid precipitate was extracted with five 200 ml. portions of ether. The combined ether extracts were dried over magnesium sulfate and concentrated to an oil. Distillation under reduced pressure gave an oil which was converted to the hydrochloride salt. Recrystallization from acetone-ethanol mixture gave 3.6 g. (17%) of pure product which melted at 193°–194° C.

Analysis: Calculated for $C_{18}H_{25}ClF_3NO$: C,59.42; H,6.93; N,3.85.

Found: C,59.46; H,6.96; N,3.73.

EXAMPLE 10

1-Cyclopropyl-3-dimethylamino-1phenyl-1-propionyloxypropane Hydrochloride.

A stirred mixture of 6 g. (0.027 mole) of 1-cyclopropyl-3-dimethylamino-1-phenyl-1-propanol and 20 g. (0.14 mole) of potassium carbonate in 25 ml. of chloroform was treated at 0° C. with 3 g. (0.032 mole) of freshly distilled propionyl chloride in 25 ml. of chloroform over a ten-minute period. The mixture was allowed to warm to room temperature and stirring was continued for 24 hours. The reaction mixture was treated with 50 ml. of water and stirring was continued another 30 minutes. The chloroform layer was separated, dried over magnesium sulfate and evaporated under reduced pressure to an oil. An ether solution of the oil was treated with ethereal hydrogen chloride. The salt was recrystallized from isopropanol-isopropyl ether mixture (yield was 4.2 g. (50%); m.p. 162°–164° C.). The analytical sample melted at 166°–168° C.

Analysis: Calculated for $C_{17}H_{26}ClNO_2$: C,65.47; H,8.40; N,4.49.

Found: C,65.70; H,8.51; N,4.78.

EXAMPLE 11

When in the procedure of Example 10, propionyl chloride is replaced by equal molar amounts of acetyl chloride, and
butyryl chloride there are obtained 1-cyclopropyl-3-dimethylamino-1-phenyl-1-acetoxy propane, and
1-cyclopropyl-3-dimethylamino-1-phenyl-1-butryryloxy propane.

EXAMPLE 12

When in the procedure of Example 10, 1-cyclopropyl-3-dimethylamino-1-phenyl-1-propanol is replaced by equal molar amounts of 1-cyclopropyl-3-dimethylamino-1-(3-trifluoromethylphenyl)-1-propanol,
1-cyclopropyl-3-dimethylamino-1-(3-chlorophenyl)-1-propanol, and
1-cyclopropyl-3-dimethylamino-1-4-methoxyphenyl)-1-propanol, there are obtained 1-cyclopropyl-3-dimethylamino-1-(3-trifluoromethylphenyl)-1-propionyloxypropane,
1-cyclopropyl-3-dimethylamino-1-(3-chlorophenyl)-1-propionyloxypropane, and
1-cyclopropyl-3-dimethylamino-1-(4-methoxyphenyl)-1-propionyloxypropane.

Effective quantities of any of the foregoing pharmacologically active compounds of Formula I may be administered together with a pharmaceutically acceptable carrier to a living animal body for therapeutic purposes according to usual modes of administration and in usual forms such as orally, in solutions, emulsions, suspensions, pills, tablets and capsules, or intramuscularly or parenterally in the form of sterile solutions.

What is claimed is:

1. A process which comprises administering to a living animal body for its analgesic effect a compound selected from those having the formula

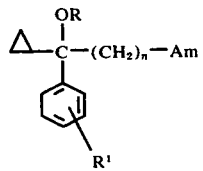

wherein;

A*m* is lower-alkylamino and di-lower-alkylamino,

R is lower alkanoyl, $R^1$ is selected from halogen, hydrogen, lower-alkoxy, lower-alkyl, and trifluoromethyl, n is selected from two and three, and the pharmaceutically acceptable acid addition salts thereof.

2. The process as defined in claim 1 wherein the active analgetic agent is 1-cyclopropyl-3-dimethylamino-1-phenyl-1-propionyloxypropane.

3. The process as defined in claim 1 wherein the active analgetic agent is 1-cyclopropyl-3-dimethylamino-1-phenyl-1-propionyloxypropane hydrochloride.

* * * * *